United States Patent
Karpowicz et al.

(10) Patent No.: US 7,270,647 B2
(45) Date of Patent: Sep. 18, 2007

(54) APPARATUS FOR VACUUM-ASSISTED IRRIGATION AND DRAINAGE OF A BODY CAVITY

(75) Inventors: John Karpowicz, Chester Springs, PA (US); Kevin P Klocek, Ardmore, PA (US)

(73) Assignee: Boehringer Technologies, L.P., Norristown, PA (US)

( * ) Notice: Subject to any disclaimer, the term of this patent is extended or adjusted under 35 U.S.C. 154(b) by 202 days.

(21) Appl. No.: 11/071,838

(22) Filed: Mar. 3, 2005

(65) Prior Publication Data

US 2005/0197645 A1 Sep. 8, 2005

Related U.S. Application Data

(60) Provisional application No. 60/549,973, filed on Mar. 4, 2004.

(51) Int. Cl.
*A61M 1/00* (2006.01)
*A61M 37/00* (2006.01)

(52) U.S. Cl. .................. 604/35; 604/34; 604/132; 604/133

(58) Field of Classification Search ............ 604/334, 604/335, 37, 128, 132, 276, 247, 249, 118, 604/119, 33, 35, 30, 19, 27, 34; 128/207.14, 128/307.16
See application file for complete search history.

(56) References Cited

U.S. PATENT DOCUMENTS

| | | | | |
|---|---|---|---|---|
| 5,269,756 | A | * | 12/1993 | Dryden ..................... 604/171 |
| 5,354,267 | A | * | 10/1994 | Niermann et al. ............ 604/32 |
| 2003/0153897 | A1 | * | 8/2003 | Russo ....................... 604/537 |
| 2004/0133149 | A1 | | 7/2004 | Haischmann et al. |

* cited by examiner

*Primary Examiner*—Kevin C. Sirmons
*Assistant Examiner*—Elizabeth MacNeill
(74) *Attorney, Agent, or Firm*—RatnerPrestia

(57) ABSTRACT

A system and method to administer a liquid agent into a body cavity of a patient is provided. One exemplary system comprises a lumen disposed into an airway of the patient and a valve assembly coupled to the lumen. The valve assembly comprises a body portion, a first port and a second port. A pump assembly for receiving the liquid agent is coupled to the valve assembly in a fluid tight relationship. The pump assembly provides the liquid to the lumen through the first port of the valve assembly. The liquid along with a portion of secretions generated by the patient are extracted through the lumen and flow out of said valve assembly through the second port for disposal responsive to a natural body function and/or a vacuum from a vacuum source. One exemplary method comprises the steps of disposing a lumen into the body cavity of the patient, the lumen comprising a fluid port; introducing the liquid agent into the body cavity through the fluid port; and extracting at least the liquid from the body cavity through the fluid port responsive to a natural body function and/or a vacuum from the vacuum source.

16 Claims, 3 Drawing Sheets

APPARATUS FOR VACUUM-ASSISTED IRRIGATION AND DRAINAGE OF A BODY CAVITY

CROSS REFERENCE TO RELATED APPLICATIONS

This application claims the benefit of priority to U.S. Provisional Patent Application No. 60/549,973, filed on Mar. 4, 2004, the contents of which are incorporated in this application by reference.

FIELD OF THE INVENTION

This invention relates to devices and methods for irrigating and draining body cavities with vacuum. More specifically, this invention relates to applications where the irrigation and aspiration of body cavities of a patient, such as the subglotic region of a patient on mechanical ventilation can be a beneficial aid to reducing the risk of pneumonia acquired as a result of such mechanical ventilation.

BACKGROUND OF THE INVENTION

Critically ill patients often require life support in the form of mechanical ventilation. Ventilated patients receive an artificial airway in the form of an Endotracheal Tube or Tracheostomy Tube. The artificial airway is placed in the trachea and a distal cuff is inflated to seal the trachea to receive mechanical ventilation. The artificial airway cuff is placed just below the vocal cords and the glottis. It has been known that patients on mechanical ventilation are at increased risk of developing Ventilator Associated Pneumonia (VAP). Recent studies have shown reductions in the incidence of VAP when artificial airways that incorporate an aspiration tube are employed. Use of these newer artificial airways reduce the incidence of VAP and delay onset of VAP, but improvement is still required. Additionally, the artificial airway is an imperfect barrier to bacteria colonies that inhabit the mouth, throat and stomach, and interrupts the body's natural defense mechanism. Methods that at least partially restore the natural action of expectoration are expected to improve care.

Subglottic secretions that are encountered in the airway can be very thick and persistent and present a challenge for removal via the conventional passages in the artificial airways. Adding additional lumens to artificial airways is not practical, because concern exists over the available space in the patient's throat.

SUMMARY OF THE INVENTION

In view of the shortcomings of conventional systems and methods, a system to administer a liquid agent into a body cavity of a patient for use with a vacuum source is provided.

According to one aspect of the present invention, the system comprises a lumen which is disposed into an airway of the patient; a valve assembly comprising a body portion, a first port and a second port, with the first port coupled; and a pump assembly coupled to the valve assembly in a fluid tight relationship, with the pump assembly receiving the liquid agent. The pump assembly provides the liquid to the lumen through the first port of the valve assembly, and at least the liquid is extracted through the lumen and flows out of the valve assembly through the second port.

According to another aspect of the present invention, the valve assembly further comprises a first passage coupled between the first outlet port and the second outlet port; a second passage coupled to the first passage, the second passage substantially orthogonal to the first passage; a poppet slideably disposed within the second passage, the poppet having a substantially "L" shaped passage from an end surface to a sidewall of the poppet; a resilient member coupled between a portion of the poppet and an end portion of the valve, the resilient member exerting a force on the poppet; and a projection disposed at a lower surface of the first passage.

According to a further aspect of the present invention, the poppet is disposed within the first passage such that the "L" shaped passage communicates the liquid from the pump assembly into the first port of the valve assembly under a force from the pump assembly.

According to still another aspect of the present invention, the system further comprising a receptacle having an inlet port coupled to the second port of the valve assembly and an outlet port coupled to the vacuum source, the receptacle receiving at least the fluid from the lumen in response to an urging by a vacuum from the vacuum source.

According to yet another aspect of the present invention, the pump assembly provides the liquid to the lumen through the first port of the valve assembly as an interior volume of the pump assembly is reduced, and at least the liquid is extracted through the lumen and flows out of the valve assembly through the second port as the interior volume of the pump assembly increases.

According to still a further aspect of the present invention, the system comprises a lumen disposed into the body cavity of the patient, the lumen comprising a fluid port; a valve assembly comprising a body portion, a first port and a second port, the first port coupled to the lumen; and a pump assembly coupled to the valve assembly in a fluid tight relationship, the pump assembly for receiving the liquid agent and transferring the liquid agent to the valve assembly, wherein the pump assembly provides the liquid to the fluid port in a first direction through the valve assembly, and at least the liquid flows through the fluid port in a second direction opposite to the first direction.

According to a method aspect of the present invention, a procedure for administering a liquid agent into a body cavity of a patient is provided. The method comprises the steps of disposing a lumen into the body cavity of the patient, where the lumen comprising a fluid port; introducing the liquid agent into the body cavity through the fluid port; and extracting at least the liquid from the body cavity through the fluid port responsive to a vacuum from a vacuum source and/or a natural flow from the patient.

According to another aspect of the present invention, the method further comprises the steps of introducing a further liquid agent into the body cavity through the fluid port; and extracting at least the further liquid from the body cavity through the fluid port responsive to a vacuum from a vacuum source and/or a natural flow from the patient.

According to a further aspect of the present invention, the liquid agent is a cleansing agent for introduction into the aspiration channel of the artificial airway. Cleansing agents may include but are not limited to water, saline, antibiotic solutions, solutions containing silver ions, surfactants, enzyme dissolving liquids, mouthwash etc., for example.

According to yet another aspect of the present invention, vacuum is used to subsequently remove a bolus of fluid along with any secretions or pathogens that are diluted and mobilized in the subglottic region.

According to still another aspect of the present invention, a controllable suction source is utilized to administer safe levels of vacuum. The delivery of the cleansing agent is intended to be initiated by a health care practitioner in the course of patient care, but can be programmed into the exemplary device in order to be carried out automatically on predetermined timed intervals as required. The delivery action once initiated is automatic in that the irrigation and aspiration occur subsequent to each other following an established protocol.

According to still another aspect of the present, invention, the cleansing fluid is provided in pulses.

These and other aspect will become apparent in view of the following description.

BRIEF DESCRIPTION OF THE DRAWINGS

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawing are the following Figures.

DETAILED DESCRIPTION OF THE INVENTION

Figure 1:
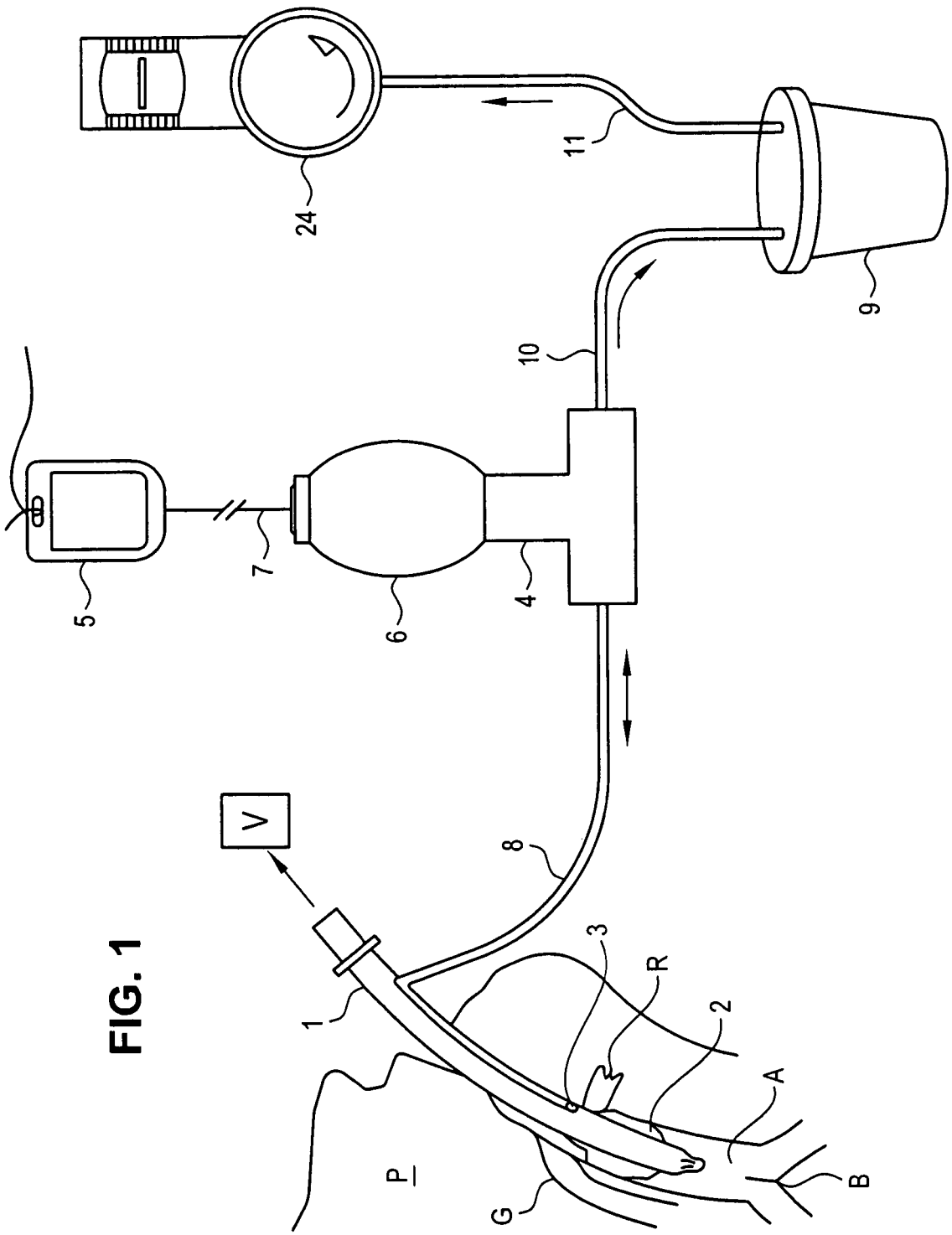
FIG. 1 is a diagram illustrating a system according to an exemplary embodiment of the present invention.

FIG. 1 illustrates a system according to an exemplary of the present invention. As shown in FIG. 1, patient P is mechanically ventilated by ventilation source V via a lumen, such as endotracheal tube (elongate member) 1. Endotracheal tube 1 is desirably placed in the trachea above the bronchial bifurcation B and below the glottis G. An inflatable balloon or cuff 2 is inflated to seal the breathing tube in the patient's airway A. The region R, defined by the space above the proximal end of the cuff and the glottis, refers to the subglottic space and is the area of attention for the exemplary device. Endotracheal tube 1 is a modified device and contains an aspiration port 3 used to evacuate the subglottic space. One type of endotracheal tube 1 that may be used is the HI-LO Evac ET Tube manufactured by TYCO Healthcare/Mallinkrodt of Hazelwood, Mo. Current use of the endotracheal tube involves either continuous or intermittent suction to remove the fluids that accumulate in the subglottic space.

There are specific problems associated with only aspiration techniques, in that the secretions are often very tenacious and resist aspiration through a small orifice such as is shown. It has been determined that irrigating and aspirating has distinct advantages in the process. Irrigation tends to liquefy secretions and enable efficient removal. Irrigation also mobilizes microorganisms and allows for more efficient removal of potentially pathogenic organisms.

The Mallinkrodt Artificial airway is effectively improved by incorporating the following additional capability. A source of cleansing solution 5 such as saline or saline with an antibiotic is attached to a pumping device such as a squeeze bulb assembly 6 via fluid line 7. Other well-known pumping devices, such as a bellows, a spring returned syringe or a programmable syringe pump are readily envisioned as well. Squeeze bulb assembly 6 is attached to a directional valve 4. Operation of directional valve 4 is described in detail below.

The aspiration port 3 on endotracheal tube 1 is attached to directional valve 4 via tube 8. Directional valve 4 is in turn attached to waste receptacle 9 via suction tubing 10. Waste canister 9 is in turn attached to a suction control 24 via tubing 11. Suction control 24 is attached to Hospital wall suction (not shown) and maintains a low continuous vacuum or can be intermittent in nature.

Safety of the overall system must address the concern over administering an excess amount of fluid that could possibly result in excess fluid infiltration into the lungs of the patient. Placing fluid source 5 at or below the point where the aspiration port 3 of the artificial airway exits will effectively safety the system. Placement of the directional valve 4 below the patient's subglottic region is desirable and will encourage a siphon action in the direction of waste receptacle 9. By enabling function through a single lumen, the risk associated with an occluded line or entry port is addressed by the exemplary embodiment of the present invention because clogs are readily dispersed by the injection of fluids. A large amount of debris is addressed by allowing for an excess of fluid to be administered to the subglottic region, thus encouraging overflow into the esophagus where autonomic swallowing can remove fluids. There is anticipated benefit of rinsing the esophagus with a solution. The manual aspects of the present invention address a failure in the actuation of the artificial airway cuff 2. Further redundancy may be incorporated by providing a pneumatic relay, for example, to desirably prevent the administration of fluid in the absence of a given pressure signal from the artificial airway cuff. Additional safety features are incorporated by the design in the directional valve and squeeze bulb assembly.

Figure 2:
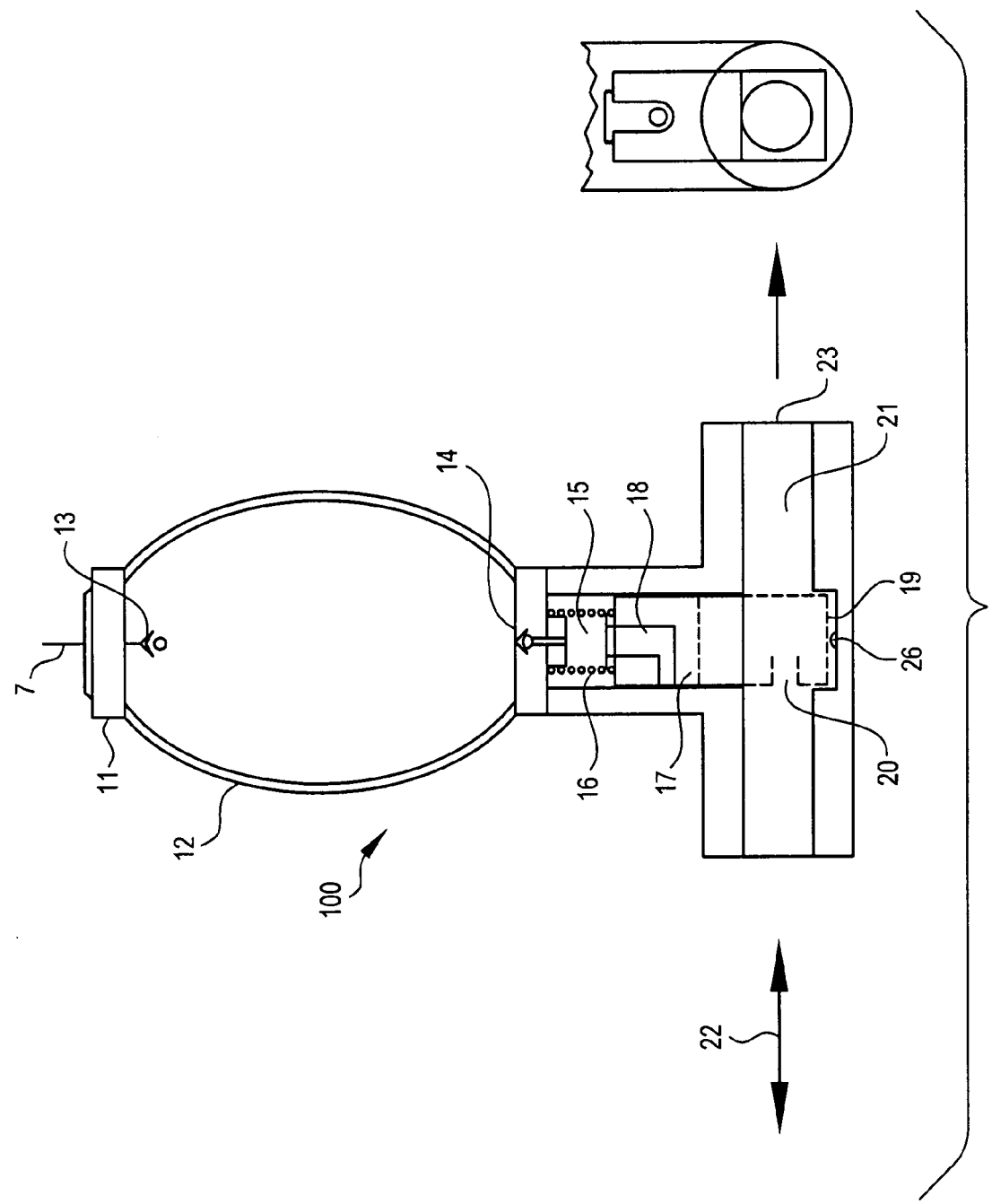
FIG. 2 is a cross-sectional view of an exemplary aspirating device of FIG. 1.

Referring now to FIG. 2 a cross-sectional view of a portion of the system is illustrated. As shown in FIG. 2, irrigation/aspiration assembly 100 comprising squeeze bulb assembly 6 and directional valve 4 functions as follows. Fluid source 5 is attached to cap 11 via tubing 7. Cap 11 is coupled to the top portion of bulb 12, formed preferably from an elastic material. Bulb 12 is squeezed, either manually or under mechanical control (not shown), to urge the flow of fluid from fluid source 5 into the interior of bulb 12. A bellows, syringe or other similar apparatus will function as well. Inlet check valve 13 coupled to an end of tubing 7, such as a duckbill for example, prevents reverse flow of the fluid back into fluid source 5. Although illustrated as disposed within bulb 12, check valve 13 may be incorporated at any point along tubing 7 as desired. Similarly, outlet check valve 14 disposed at a lower portion of bulb 12 ensures unidirectional flow out of bulb 12. Outlet check valve 14 provides a redundant function to prevent filling of squeeze bulb 12 from the patient side of the squeeze bulb, The outlet of bulb 12 is directed past valve 14 to an interior chamber 15. Within chamber 15 is spring 16 that in turn is attached to a poppet valve 17. A non-limiting example of spring 16 is an extension type spring. Poppet valve 17 has a passage 18 that is directed at substantially a right angle.

Upon squeezing of bulb 12, an elevated pressure is generated in chamber 15 causing poppet valve 17 to move into the position as shown by dotted lines 19. Outlet 20 of poppet valve 17 is directed towards aspiration port 3 of the patient's artificial airway. The port of poppet valve 17 is positioned such that the entire internal passage 21 of valve body 25 is essentially occluded before the outlet 20 is exposed, thus ensuring that the majority of the fluid is expelled in the direction of the artificial airway as shown by bidirectional arrow 22. The opposite end 23 of valve body 25 is directed toward waste receptacle 9 where aspirates and irrigating fluids are accumulated. Once pressure is relieved, either due to the complete emptying of bulb 12 or the release of hand pressure, spring 16 returns poppet 18 to its retracted position, thus restoring an essentially obstruction free passage for the removal of the now diluted aspirate and contents of the subglottic space.

Other spring return mechanisms for the poppet valve 17 are readily envisioned. Additionally, the clearance between the poppet valve 17 and the interior chamber 15 can be so constructed as to allow free movement of the poppet valve 17, but not allow fluid flow. Typically, limiting the total diametral clearance to less than 0.001" is sufficient to provide a fluid tight seal for the ranges of pressures encountered on this device. This construction further enhances safety with regard to the delivery of excess fluid. Features are directed to the risk of aspirated material causing the valve to stick, such as making the valve from Teflon material and shielding surfaces that could adhesively stick from aspirated liquids. Directional valve body 25 may include a knob or button 26 that minimizes the surface area that could be adhesively joined by poppet valve 17 when in position 19, thus preventing poppet valve 17 from failing in the open position.

It is anticipated that the volume of the bulb 12 be optimized to effectively administer sufficient volume to the aspiration site in the subglottic region as to optimally cleanse the space. Multiple cleansing steps are readily applied sequentially and/or at predetermined intervals as determined by clinical need. Pressure pulses to dislodge the more persistent secretions can augment cleansing actions. Multiple systems could be arranged to allow administration of a first cleansing agent followed by a rinsing agent.

The system described here is essentially a manual device where a health care professional periodically performs the intervention. An automatic system that provides regular intervention is readily conceived employing the embodiments of the directional valve 4. Multiple valves could also be arranged, as desired, so as to facilitate the programmable administration of a sequence of desirable solutions.

Irrigation and aspiration through a single line (such as line 8 shown in the exemplary embodiment) serves to reduce problems associated with clogging of the aspiration line or the inlet to said line.

Regular irrigation of the subglottic area has been shown to minimize the trauma associated with extubation of the artificial airway. Additional benefits are derived by rinsing the upper airway with solution that can aid in oral care and wash excess materials into the GI tract.

It is further anticipated that conscious but intubated patients could benefit from the ability to inject fluid into their own throats for the sake of comfort.

Figure 3:
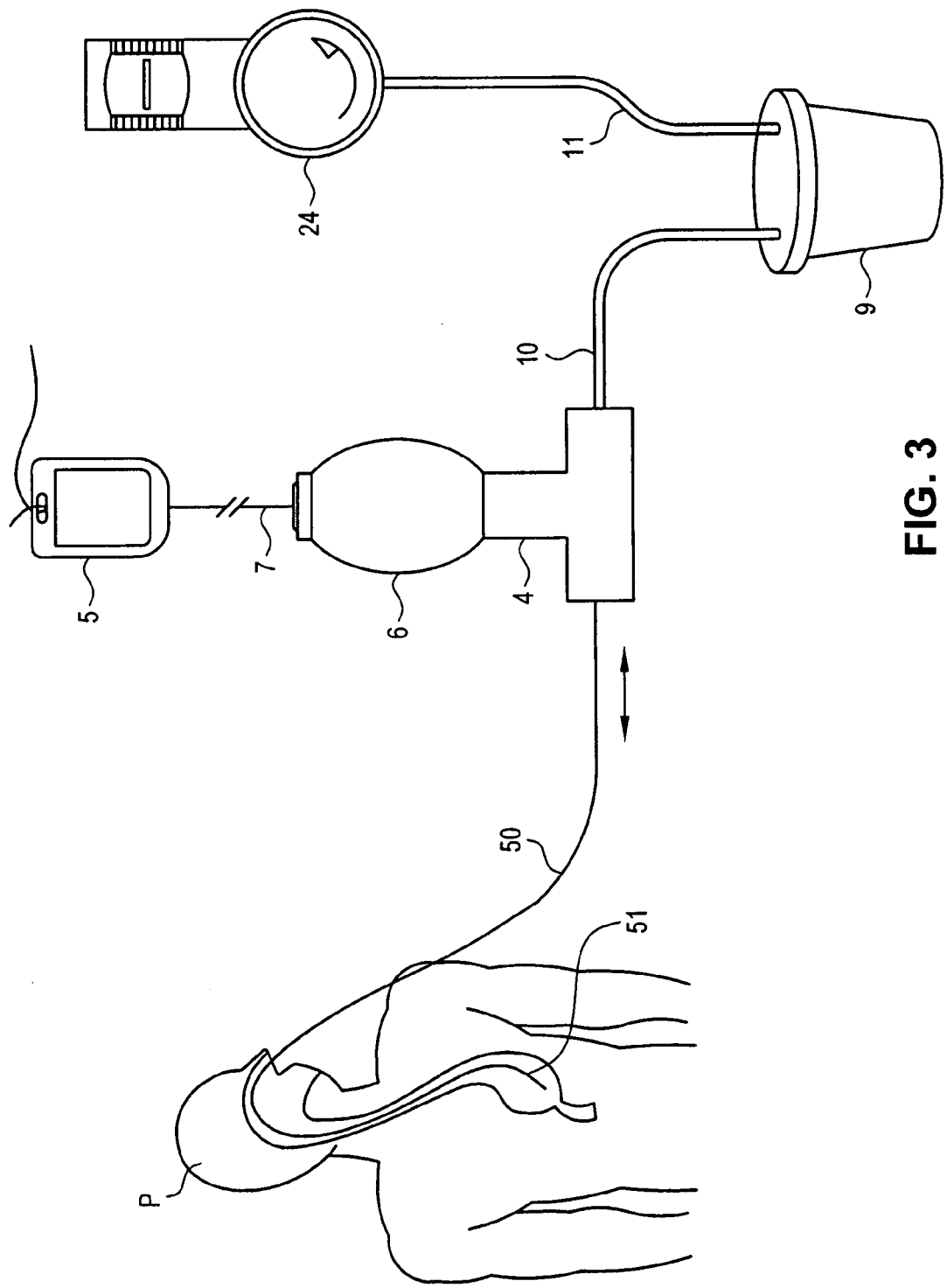
FIG. 3 is a diagram illustrating a system according to another exemplary embodiment of the present invention.

Additional clinical applications would benefit from the unique capabilities of the invention such as irrigating a suction catheter that has been placed in the gastric space via a naso-gastric suction catheter. FIG. 3 illustrates an alternate embodiment where the periodic introduction of a retrograde flow of a fluid bolus will serve to irrigate and unclog an evacuation tube that has been placed in a patient's stomach. As shown in FIG. 3, Patient P is attached to the exemplary system illustrated in FIG. 1 except that directional valve 4 is connected to naso-gastric (NG) drainage tube 50, which is in turn passed through the nasal cavity and down to the stomach 51 of patient P. The naso-gastric tubes functions to remove air, fluid and some debris from the gastric space. In conventional systems this tube is prone to clogging with foreign matter, and the inlet ports that are disposed around the distal end of the tube (not shown) often become attached to the inner wall of the stomach. Periodic irrigation would benefit the patient by ensuring a patent fluid path. The process for introducing the fluid from fluid source 5 into the body cavity (in this case stomach 51) and extracting the waste fluid into waste receptacle 9 is the same as that described above with respect to the first exemplary embodiment and is not repeated here.

The techniques described herein also afford the advantage of establishing a closed system that minimizes the periodic access that often results in a so-called break in technique that has the risk of introducing pathogens.

A similar irrigation assembly can be applied to a closed surgical wound, such as encountered following joint replacement surgery, where it is desirable to periodically bathe the operative site with an antibiotic without adding an additional catheter line. Open wounds such as burns would also benefit from the periodic application of a cleansing or curative substance to the wound site that is treated with a vacuum system.

Arthroscopic surgical techniques employ irrigation and aspiration methods and heretofore it has not been possible to direct a source of irrigating solution in the retrograde direction to the suction flow.

The invention may also be placed in the collection circuit of a Foley urinary catheter to apply a retrograde fluid bolus such as a contrast media into the flowing urine stream. Although the aforementioned embodiments are illustrated for the treatment of humans, the invention is not so limited as it is contemplated that animals may also benefit for these treatment systems and methods.

According to still another aspect of the present invention, to ease the process of extubation by minimizing the accumulation of aspirate that can partially solidify and cause the artificial airway to be semi-permanently attached.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A system to administer a liquid agent into a body cavity of a patient for use with a vacuum source, said system comprising:
    an elongate member having a lumen disposed into the body cavity of the patient;
    a valve assembly comprising:
        a body portion,
        a first port and a second port, said first port coupled to said lumen,
        a first passage coupled between said first port and said second port,
        a second passage coupled to said first passage, said second passage substantially orthogonal to said first passage,
        a poppet laterally slideably disposed within said second passage, said poppet having a substantially "L" shaped passage from an end surface to a sidewall of said poppet; and
    a pump assembly coupled to said valve assembly in a fluid tight relationship, said pump assembly adapted for receiving the liquid agent, wherein said pump assembly provides the liquid to said lumen through said first port of said valve assembly, and automatically permits at least the liquid to be extracted through said lumen and flows out of said valve assembly through said second port.

2. The system according to claim 1, wherein said valve assembly further comprises:
   a resilient member coupled between a portion of said poppet and an end portion of said valve, said resilient member exerting a lateral force on said poppet; and
   a projection disposed at a lower surface of said first passage.

3. The system according to claim 1, wherein said first port is a bidirectional port and said second port is a unidirectional port, a flow from said second port exiting said valve.

4. The system according to claim 1, further comprising a receptacle having an inlet port coupled to said second port of said valve assembly and an outlet port coupled to said vacuum source, said receptacle receiving at least the fluid from said second port in response to a pressure differential created by the vacuum source.

5. The system according to claim 1, wherein said pump assembly is a positive displacement pump, a syringe pump or a resilient vessel.

6. The system according to claim 1, wherein said pump assembly is under manual control.

7. The system according to claim 1, wherein said pump assembly is under automatic control.

8. The system according to claim 1, wherein said system is programmable.

9. The system according to claim 1, wherein the liquid agent is at least one of water, saline, saline in combination with an antibiotic, a solution containing silver ions, a surfactant, an enzyme dissolving liquids, and/or mouthwash.

10. The system according to claim 1, wherein said aspiration port is disposed adjacent a glottis of the patient.

11. The system according to claim 1, wherein at least a portion of secretions generated by the patient are extracted with said fluid through said aspiration port.

12. The system according to claim 1, wherein said flow through said lumen is responsive to a natural flow from the patient and/or responsive to a vacuum from a vacuum source.

13. The system according to claim 1, wherein said body cavity is at least one of a substantially closed surgical site, a gastric cavity, a pulmonary cavity, and/or a urinary tract.

14. The system according to claim 1, wherein the patient is a human or an animal.

15. The system according to claim 2, wherein said projection is adapted to provide a predetermined spaced relationship between a bottom portion of said poppet and a lower surface of said second passage to prevent said poppet from sealing against said lower surface.

16. A system to administer a liquid agent into a body cavity of a patient for use with a vacuum source, said system comprising:
   an elongate member having a lumen disposed into the body cavity of the patient;
   a valve assembly comprising a body portion, a first port and a second port, said first port coupled to said lumen; and
   a pump assembly coupled to said valve assembly in a fluid tight relationship, said pump assembly adapted for receiving the liquid agent,
   wherein said pump assembly provides the liquid to said lumen through said first port of said valve assembly, and permits at least the liquid to be extracted through said lumen and flows out of said valve assembly through said second port, and
   wherein said poppet is disposed within said valve assembly such that said poppet communicates the liquid from said pump assembly into said first port of said valve assembly, said poppet moving from a first position to a second position under a force from said pump assembly.

* * * * *